US010653798B2

(12) United States Patent
Hardy et al.

(10) Patent No.: US 10,653,798 B2
(45) Date of Patent: May 19, 2020

(54) ELECTROACTIVE SUPRAMOLECULAR POLYMERIC ASSEMBLIES, METHODS OF MAKING ELECTROACTIVE SUPRAMOLECULAR POLYMERIC ASSEMBLIES, AND METHOD OF USING ELECTROACTIVE SUPRAMOLECULAR POLYMERIC ASSEMBLIES

(71) Applicant: University of Florida Research Foundation, Inc., Gainesville, FL (US)

(72) Inventors: John Hardy, Bexhill-On-Sea (GB); Christine E. Schmidt, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 147 days.

(21) Appl. No.: 15/578,292

(22) PCT Filed: Jun. 1, 2016

(86) PCT No.: PCT/US2016/035227
§ 371 (c)(1),
(2) Date: Nov. 30, 2017

(87) PCT Pub. No.: WO2016/196604
PCT Pub. Date: Dec. 8, 2016

(65) Prior Publication Data
US 2018/0140718 A1    May 24, 2018

Related U.S. Application Data

(60) Provisional application No. 62/170,742, filed on Jun. 4, 2015.

(51) Int. Cl.
*A61K 47/69* (2017.01)
*C08G 73/02* (2006.01)
*A61N 1/30* (2006.01)
*A61N 1/32* (2006.01)
*C08G 69/10* (2006.01)

(52) U.S. Cl.
CPC ............ *A61K 47/6935* (2017.08); *A61N 1/30* (2013.01); *C08G 73/028* (2013.01); *A61N 1/325* (2013.01); *C08G 69/10* (2013.01); *C08G 73/0266* (2013.01)

(58) Field of Classification Search
CPC ...... A61K 47/6935; A61N 1/30; A61N 1/325; C08G 69/10; C08G 73/0266; C08G 73/028
See application file for complete search history.

(56) References Cited

U.S. PATENT DOCUMENTS

| 5,855,900 A | 1/1999 | Nobuhiko |
| 7,265,379 B2 | 9/2007 | Sandberg et al. |
| 8,247,524 B2 | 8/2012 | Janssen et al. |
| 8,529,539 B2 | 9/2013 | Weber et al. |
| 8,622,987 B2 | 1/2014 | Ismagilov et al. |
| 2003/0174377 A1 | 9/2003 | Reynolds et al. |
| 2009/0087493 A1 | 4/2009 | Dai et al. |
| 2010/0233226 A1* | 9/2010 | Ferain ................ A61K 9/0009 424/422 |
| 2011/0060280 A1 | 3/2011 | Caffey et al. |
| 2012/0289887 A1 | 11/2012 | Visco et al. |
| 2013/0338569 A1 | 12/2013 | Tsai et al. |

FOREIGN PATENT DOCUMENTS

| CN | 102659991 B | 11/2014 |
| WO | 9604340 | 2/1996 |
| WO | 2014055846 | 4/2014 |

OTHER PUBLICATIONS

El-Faham et al. (Chemistry Central Journal 2012,6:128 1-10) (Year: 2012).*
Guo et al. (Progres in Polymer Science 38 (2013) 1263-1286, IDS) (Year: 2013).*
International Search Report for PCT/US2016/035227 dated Oct. 21, 2016.
A. S. Mandal, N. Biswas, K. M. Karim, A. Guha, S. Chatterjee, M. Behera and K. Kuotsu, Drug delivery system based on chronobiology—A review J. Controlled Release, 2010, 147, 314.
B. Chertok, M. J. Webber, M. D. Succi and R. Langer, Drug Delivery Interfaces in the 21st Century: From Science Fiction Ideas to Viable Technologies; Mol. Pharm., 2013, 10, 3531.
M. E. Caldorera-Moore, W. B. Liechty and N. A. Peppas, Responsive Theranostic Systems: Integration of Diagnostic Imaging Agents and Responsive Controlled Release Drug Delivery Carriers; Acc. Chem. Res., 2011, 44, 1061.
P. Leclere, M. Surin, P. Jonkheijm, O. Henze, A. P. H. J. Schenning, F. Biscarini, A. C. Grimsdale, W. J. Feast, E W. Meijer, K. Mullen, J. L. Bredas and R. Lazzaroni, Organic semi-conducting architectures for supramolecular electronics; Eur. Polym. J., 2004, 40, 885.
M. Berggren and A. Richter-Dahlfors, Organic Bioelectronics; Adv. Mater., 2007, 19, 3201.
Z. L. Yue, S. E. Moulton, M. Cook, S. O'Leary and G. G. Wallace, Controlled delivery for neuro-bionic devices; Adv. Drug Deliv. Rev., 2013, 65, 559.
A. Guiseppi-Elie, Electroconductive hydrogels: Synthesis, characterization and biomedical applications; Biomaterials, 2010, 31, 2701.
The Rise of Organic Bioelectronics; Jonathan Rivnay, Róiín M. Owens, and George G. Malliaras* Department of Bioelectronics, Ecole Nationale Supérieure des Mines, CMP-EMSE, MOC, 880 route de Mimet, 13541 Gardanne; 7 pages.
A. D. Bendrea, L. Cianga and I. Cianga, Review paper: Progress in the Field of Conducting Polymers for Tissue Engineering Applications; J. Biomater. Appl., 2011, 26, 3.

(Continued)

*Primary Examiner* — Anna R Falkowitz
(74) *Attorney, Agent, or Firm* — Thomas | Horstmeyer, LLP (57) ABSTRACT

Embodiments of the present disclosure provide for electroactive supramolecular polymeric assemblies, methods of making electroactive supramolecular polymeric assemblies, methods of using electroactive supramolecular polymeric assemblies, and the like.

4 Claims, 8 Drawing Sheets

(56) References Cited

OTHER PUBLICATIONS

J. G. Hardy, J. Y. Lee and C. E. Schmidt, Biomimetic conducting polymer-based tissue scaffolds; Current Opinion in Biotechnology., 2013, 24, 847-854.

B. L. Guo, L. Glavas and A. C. Albertsson, Biodegradable and electrically conducting polymers forbiomedical applications Prog. Polym. Sci., 2013, 38, 1263.

J. G. Hardy, D. J. Mouser, N. Arroyo-Currás, S. Geissler, J. K. Chow, L. Nguy, J. M. Kim and C. E. Schmidt, Biodegradable electroactive polymers for electrochemically triggered drug delivery; J. Mater. Chem. B, 2014, 2, 6809.

D. Svirskis, J. Travas-Sejdic, A. Rodgers and S. Garg; Electrochemically controlled drug delivery based on intrinsically conducting polymers; J. Control. Release, 2010, 146, 6.

V. Pillay, T. S. Tsai, Y. E. Choonara, L C. du Toit, P. Kumar, G. Modi, D. Naidoo, L. K. Tomar, C. Tyagi and V. M. Ndesendo, A review of integrating electroactive polymers as responsive systems for specialized drug delivery applications; J. Biomed. Mater. Res., A, 2014, 102, 2039.

Engineered Spider Silk Protein-Based Composites for Drug Delivery John G. Hardy, Aldo Leal-Egana, Thomas R. Scheibel; GmbH & Co. KGaA, Weinheim DOI: 10.1002/mabi.201300233 1431; Macromol. Biosci. 2013, 13, 1431-1437.

R. Dong, Y. Zhou, X. Huang, X. Zhu X, Y. Lu and J. Shen.; Functional Supramolecular Polymers for Biomedical Applications; Advanced Materials, 2015, 27, 498.

A. R. Hirst, B. Escuder, J. F. Miravet and D. K. Smith, High-Tech Applications of Self-Assembling Supramolecular Nanostructured Gel-Phase Materials: From Regenerative Medicine to Electronic Devices Angew. Chem. Int. Ed., 2008, 47, 8002.

M. Hasegawa and M. Iyoda, Conducting supramolecular nanofibers and nanorods; Chem. Soc. Rev., 2010, 39, 2420.

S. H. Kim and J. R. Parquette, A model for the controlled assembly of semiconductor peptides; Nanoscale, 2012, 4, 6940.

Reactive Supramolecular assemblies of mucopolysaccharide, polypyrrole and protein as controllable biocomposites for a new generation of biomaterials. A. J. Hodgson, K. Gilmore, C. Small, G. G. Wallace, I. L. Mackenzie, T. Aoki and N. Ogata, Supramol. Sci., 1994, 1, 77.

E. K. Schillinger, E. Mena-Osteritz, J. Hentschel, H. G. Börner and Peter Báuerle, Oligothiophene Versus b-Sheet Peptide: Synthesis and Self-Assembly of an Organic Semiconductor-Peptide Hybrid Adv. Mater. 2009, 21, 1562.

A. Digennaro, H. Wennemers, G. Joshi, S. Schmid, E. Mena-Osteritz and Peter Bäuerle, Chiral suprastructures of asymmetric oligothiophenehybrids induced by a single proline Chem. Commun., 2013, 49, 10929.

Z. Zhang, S. Wei and L. Han, Adv. Mater. Res., 2011, 284-286, 2110.

I. Rozalska, P. Kulyk and I. Kulszewicz-Bajer, Synthesis and spectroscopic properties of aniline tetramers. Comparative studies New. J. Chem., 2004, 28, 1235.

Linear 1,4-coupled oligoanilines of defined length: preparation and spectroscopic properties Izabelal. Kulszewicz-Bajer, I. Rozalska and M. Kurtyek, New. J. Chem., 2004, 28, 669.

How Controlled and Versatile is N-carboxy anyydride polymerizaation . . . G. J. M. Habraken, M. Peeters, C. H. J. T. Dietz, C. E. Koninga and A. Heise, Polym. Chem., 2010, 1, 514.

Z. Pang, J. Fu, P. Lv, F. Huang and Q. Wei, Sensors, 2014, 14, 21453.

Structural Analysis of Spider Silk Films; U. Slotta, M. Tammer, F. Kremer, P. Koelsch and T. Scheibel, Supramol. Chem., 2006, 18, 1.

Evidenced by infrared spectroscopy of the presence of F. Paquet-Mercier, T. Lefevre, M. Auger and M. Pezolet, Soft Matter, 2013, 9, 208.

O. S. Rabotyagova, P. Cebe and D. L. Kaplan, Role of Polyalanine Domains in b-Sheet Formation in Spider Silk Block Copolymers; Macromol. Biosci. 2010, 10, 49.

J. G. Hardy and T. R. Scheibel, Production and Processing of Spider Silk Proteins; J. Polym. Sci: A: Polym. Chem. 2009, 47, 3957-3963.

J. G. Hardy and T. R. Scheibel, Biochem. Soc. Trans. 2009, 37, 677.

Z. Shao, Z. Yu, Jianchen Hu, S. Chandrasekaran, D. M. Lindsay, Z. Wei and C. F. J. Faul, Block-like electroactive oligo(aniline)s: anisotropic structures with anisotropic function J. Mater Chem., 2012, 22, 16230.

Y. Wang, H. D. Tran, L. Liao, X. Duan, and R. B. Kaner, Nanoscale Morphology, Dimentional Control. J. Am. Chem. Soc., 2010, 132, 10365.

C. Gabriel, S. Gabriel and E. Corthout, The dielectric properties of biological tissues: I. Literature survey Phys. Med. Biol., 1996, 41, 2231.

S. Gabriel, R. W. Lau and C. Gabriel, The dielectric properties of biological tissues, Phys. Med. Biol., 1996, 41, 2251.

108 S. Gabriel, R. W. Lau and C. Gabriel, Phys. Med. Biol., 1996, 41, 2271.

P. H. Zeplin, N. C. Maksimovikj, M. C. Jordan, J. Nickel, G. Lang, A. H. Leimer, L. Römer and T. Scheibel, Adv. Fund. Mater., 2014, 24, 2658.

C. Vallejo-Giraldo, A. Kelly, M. J. Biggs, Biofunctionalisation of electrically conducting polymers; Drug. Discov. Today, 2014, 19, 88.

H. Shin, S. Jo and A. G. Mikos, Biomimetic materials for tissue engineering Biomaterials, 2003, 24, 4353.

K. G. Sreejalekshmi and P. D. Nair, J. Biomed. Mater. Res. Part A, 2011, 96A, 477.

K. I. Umehara, T Iwatsubo, K. Noguchi, T. Usui and H. Kamimura, Xenobiotica, 2008, 38, 1203.

Biomimetic conducting polymer-based tissue scaffolds John G Hardy1,4, Jae Y Lee2,4 and Christine E Schmid; Current Opinion in Biotechnology 2013, 24:847-854.

Balint, Caddity; Conductive polymers: Towards a smart biomaterial for tissue engineering Richard Balint a School of Materials, Faculty of Engineering and Physical Sciences, University of Manchester, Manchester M1 7HS, UK 13 pages.

\* cited by examiner

ELECTROACTIVE SUPRAMOLECULAR POLYMERIC ASSEMBLIES, METHODS OF MAKING ELECTROACTIVE SUPRAMOLECULAR POLYMERIC ASSEMBLIES, AND METHOD OF USING ELECTROACTIVE SUPRAMOLECULAR POLYMERIC ASSEMBLIES

CROSS-REFERENCE TO RELATED APPLICATIONS

This application is the 35 U.S.C. § 371 national stage application of PCT Application No. PCT/US2016/035227, filed Jun. 1, 2016, where the PCT claims the benefit of and priority to U.S. Provisional Application Ser. No. 62/170,742, having the title "ELECTROACTIVE SUPRAMOLECULAR POLYMERIC ASSEMBLIES, METHODS OF MAKING ELECTROACTIVE SUPRAMOLECULAR POLYMERIC ASSEMBLIES, AND METHODS OF USING ELECTROACTIVE SUPRAMOLECULAR POLYMERIC ASSEMBLIES," filed on Jun. 4, 2015, both of which are herein incorporated by reference in their entireties.

BACKGROUND

Technologies that enable precise control of the amount of drugs in the blood stream or specific tissues facilitate the maintenance of the amount of drug within the therapeutic window, and controlling the chronopharmacology of a drug are particularly useful for the treatment of diseases with specific chronobiologies. Thus there is a need for material to accomplish these and other similar goals.

SUMMARY

Embodiments of the present disclosure provide for electroactive supramolecular polymeric assemblies, methods of making electroactive supramolecular polymeric assemblies, methods of using electroactive supramolecular polymeric assemblies, and the like.

An embodiment of the present disclosure includes an electroactive supramolecular polymeric assembly, among others, that includes: an electroactive ABA block copolymer, where A is a non-electroactive polymer and B is an electroactive polymer.

An embodiment of the present disclosure includes an electroactive supramolecular polymeric assembly, among others, that includes: an electroactive ABA block copolymer and an agent, where A is a non-electroactive polymer and B is an electroactive polymer, wherein A is a non-electroactive oligoalanine and B is an electroactive oligoaniline, wherein the agent is selected from the group consisting of: a drug, a therapeutic agent, a radiological agent, a chemological agent, a small molecule drug, a biological agent, and combinations thereof.

An embodiment of the present disclosure includes a method of delivering an agent, among others, that includes: providing an electroactive ABA block copolymer including an agent to a subject; providing an electrical stimulus to the electroactive ABA block copolymer; and releasing the agent, wherein application of the electrical stimulus causes the agent to be released from the electroactive ABA block copolymer.

Other assemblies, compositions, methods, features, and advantages will be or become apparent to one with skill in the art upon examination of the following drawings and detailed description. It is intended that all such additional assemblies, compositions, apparatus, methods, features and advantages be included within this description, be within the scope of the present disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 4A-D shows adhesion of human dermal fibroblasts on various surfaces after 4 days in culture: FIG. 4A) Undoped MTT1, FIG. 4B) CSA-doped MTT1, FIG. 4C) Undoped MTT2, and FIG. 4D) CSA-doped MTT2. Live cells were stained green by calcein and dead cells were stained red by ethidium using a LIVE/DEAD® Viability/Cytotoxicity Kit. Scale bars represent 100 µm.

FIGS. 5A-D are FTIR spectra of the electroactive molecular tongue twisters: FIG. 5A) MTT1 undoped, FIG. 5B) MTT1 doped with CSA, FIG. 5C) MTT2 undoped, and FIG. 5D) MTT2 doped with CSA.

FIGS. 6A-D are XRD spectra of the electroactive molecular tongue twisters: FIG. 6A) MTT1 undoped, FIG. 6B) MTT1 doped with CSA, FIG. 6C) MTT2 undoped, and FIG. 6D) MTT2 doped with CSA.

FIG. 8A is a voltammogram of 0.6 mM ferrocenemethanol in 0.1 M KCl. Scan rate=10 mV $s^{-1}$. See the literature or a comparison: A. Heras, A. Colina, J. Lopez-Palacios, A. Kaskela, A. Nasibulin, V. Ruiz, E. Kauppinen, Electrochem. Commun. 2009, 11, 442-445.

DETAILED DESCRIPTION

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method may be carried out in the order of events recited or in any other order that is logically possible.

Embodiments of the present disclosure will employ, unless otherwise indicated, techniques of organic chemistry, biochemistry, microbiology, molecular biology, pharmacology, medicine, and the like, which are within the skill of the art. Such techniques are explained fully in the literature.

Prior to describing the various embodiments, the following definitions are provided and should be used unless otherwise indicated.

Unless otherwise defined, all technical and scientific terms used herein have the same meaning as commonly understood by one of ordinary skill in the art of microbiology, molecular biology, medicinal chemistry, and/or organic chemistry. Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

By "administration" is meant introducing an electroactive supramolecular polymeric assembly of the present disclosure into a subject. The route of administration can include any route of administration, such as intravenous oral, topical, subcutaneous, peritoneal, intraarterial, inhalation, vaginal, rectal, nasal, introduction into the cerebrospinal fluid, or instillation into body compartments can be used.

The terms "therapeutically effective amount" and "an effective amount" are used interchangeably herein and refer to that amount of an agent being administered that is sufficient to effect the intended application including, but not limited to, condition treatment. For example, an effective amount of the agent will relieve to some extent one or more of the symptoms of the condition being treated, and/or that amount that will prevent, to some extent, one or more of the symptoms of the disease that the host being treated has or is at risk of developing.

The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The specific dose will vary depending on the particular agent chosen, the dosing regimen to be followed, whether it is administered in combination with other agents, timing of administration, the tissue to which it is administered, and the physical delivery system in which it is carried.

The term "unit dosage form," as used herein, refers to physically discrete units suitable as unitary dosages for human and/or animal subjects, each unit containing a predetermined quantity of the agent calculated in an amount sufficient to produce the desired effect in association with a pharmaceutically acceptable diluent, carrier or vehicle. The specifications for unit dosage forms depend on the particular agent employed, the route and frequency of administration, and the effect to be achieved, and the pharmacodynamics associated with each agent in the subject.

As used herein, a "pharmaceutical composition" and a "pharmaceutical formulation" are meant to encompass embodiments of the present disclosure or agent suitable for administration to a subject, such as a mammal, especially a human. In general, a "pharmaceutical composition" or "pharmaceutical formulation" is sterile, and preferably free of contaminants that are capable of eliciting an undesirable response within the subject (e.g., the agent or the polymer assembly in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

As used herein, the terms "treatment", "treating", and "treat" are defined as acting upon a condition with an agent to reduce or ameliorate the pharmacologic and/or physiologic effects of the condition and/or its symptoms. "Treatment", as used herein, covers any treatment of a condition in a subject (e.g., a mammal, typically a human or non-human animal of veterinary interest), and includes: (a) reducing the risk of occurrence of the condition in a subject determined to be predisposed to the condition but not yet diagnosed with the condition (b) impeding the development of the condition, and (c) relieving the condition, i.e., causing regression of the condition and/or relieving one or more condition symptoms. "Treatment" is also meant to encompass delivery of agent or polymer assembly to provide a pharmacologic effect, even in the absence of a condition. For example, "treatment" encompasses delivery of an agent or polymer assembly that provides for enhanced or desirable effects in the subject.

As used herein, the terms "prophylactically treat" and "prophylactically treating" refer completely or partially preventing a condition or symptom thereof and/or may be therapeutic in terms of a partial or complete cure for a condition and/or adverse effect attributable to the condition.

As used herein, the term "subject" includes humans, mammals (e.g., cats, dogs, horses, etc.), birds, and the like. Typical subjects to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. In some embodiments, a system includes a sample and a host. The term "living subject" refers to the entire subject or organism and not just a part excised (e.g., a liver or other organ) from the living subject.

The term "sample" can refer to a tissue sample, cell sample, a fluid sample, and the like. The sample may be taken from a host. The tissue sample can include hair (including roots), buccal swabs, blood, saliva, semen, muscle, or from any internal organs. The fluid may be, but is not limited to, urine, blood, ascites, pleural fluid, spinal fluid, and the like. The body tissue can include, but is not limited to, skin, muscle, endometrial, uterine, and cervical tissue. In the present disclosure, the source of the sample is not critical.

Supramolecular polymer assemblies are a class of polymers in which the "monomers" of the polymers are held together by non-covalent interactions (e.g., hydrogen bonds, π-π stacking, solvophobic interactions, and combinations thereof).

Discussion:

Embodiments of the present disclosure provide for electroactive supramolecular polymeric assemblies, methods of making electroactive supramolecular polymeric assemblies, methods of using electroactive supramolecular polymeric assemblies, and the like. An embodiment of the electroactive supramolecular polymeric assembly can include electroactive ABA block copolymers that are conductive upon the application of an electrical stimulus. In an embodiment, an agent such as a drug can be associated with (e.g., bonded or bound by) the electroactive supramolecular polymeric assembly. In this way, embodiments of the present disclosure can be used to deliver an agent such as a drug with clinically relevant chronopharmacologies by applying an electrical stimulus at a particular time and/or location, which can facilitate the treatment of conditions with specific chronobiologies (e.g., infectious diseases, pain) as well as other conditions. In addition, embodiments of the electroactive supramolecular polymeric assemblies can be designed to control the release profiles and cell-biomaterial interactions.

Embodiments of the electroactive supramolecular polymeric assembly can include electroactive ABA block copolymers. In an embodiment, the electroactive ABA block copolymer can include a non-electroactive polymer (e.g., oligomers such as oligoalanines) as block A and an electroactive polymer (e.g., oligomers such as oligoanilines) as block B. In an embodiment, the ratio of non-electroactive oligomers to electroactive oligomers in the block copolymer can be about 1:2 to 2:1. Methods of synthesis of ABA block copolymers are provided in Example 1.

An electroactive polymer responds to an electrical stimulus (e.g., a stimulus that actuates, conducts, facilitates ion transport, and/or alters the oxidation state of the electroactive polymer). In an embodiment, the electroactive polymer can include aniline, furan, pyrrole, thiophene, porphyrin, ferrocene, or other units that yield an electroactive product. In an embodiment that includes oligoaniline, the oligoaniline can include 1 to 10,000 aniline monomers.

An electrical stimulus can include: contact (which includes contact in close proximity so that the assembly receives the electrical stimulus as well as direct contact to the electroactive polymer) of the material with a power source via a wire; wireless energy transfer, magnetic force, mechanical force, light, and/or a chemical that alters the redox state of the material. In an embodiment, the electrical stimulus is in direct contact with the material with the power source. In an embodiment, the electrical stimulus is in contact with the material with the power source so that the assembly receives the electrical stimulus where the direct contact may be a short distance away from the assembly. In an embodiment, wireless energy transfer is indirect contact of the power source with the electroactive polymer.

A non-electroactive polymer does not respond to the electrical stimulus in the same manner as the electroactive polymer responds. In an embodiment, the non-electroactive polymer can be non-degradable or degradable, and can include polyamides/proteins (e.g., polyalanine, oligoalanine, collagen, and silk), polyesters (e.g. polycaprolactone and PLLA), polysaccharides (cellulose, chitin, chitosan), DNA, RNA, polymers (e.g., polyethylyne glycol) or other units that yield a non-electroactive product. In an embodiment that includes oligoalanine, the oligoalanine can include 1 to 2000 alanine monomers.

In an embodiment, the ABA block copolymer can have the following structure:

where n is 2 to 10,000 and m+p is 2 to 20,000. In particular embodiments, n is 4 and m+p is 10 or n is 6 and m+p is 26.

In an embodiment, the electroactive supramolecular polymeric assembly can include one or more agents (e.g., a chemical or biological agent), where the agent can be disposed indirectly or directly (e.g., bound or independently suspended) on the electroactive supramolecular polymeric assembly. In particular, the agent can include, but is not limited to, a drug, a therapeutic agent, a radiological agent, a chemological agent, a small molecule drug, a biological agent (e.g., polypeptides (e.g., proteins such as, but not limited to, antibodies (monoclonal or polyclonal)), antigens, nucleic acids (both monomeric and oligomeric), polysaccharides, haptens, sugars, fatty acids, steroids, purines, pyrimidines, ligands, aptamers, and cells) and combinations thereof, that can be used to image, detect, study, monitor, evaluate, treat, and/or screen a condition (e.g., a disease, an infection, an injury, or a related biological event) of the subject.

In an embodiment, the agent is included in an effective amount to accomplish its purpose (e.g., therapeutically effective amount), can depend upon a variety of factors, including for example, the age, body weight, general health, sex, and diet of the subject; the time of administration; the route of administration; the rate of excretion of the agent employed; the duration of the treatment; the existence of other drugs used in combination or coincidental with the specific composition employed; and like factors well known in the medical arts.

In general, the agent can be bound to the electroactive supramolecular polymeric assembly by a physical, biological, biochemical, mechanical, and/or chemical association directly or indirectly by a suitable means. The term "bound" can include, but is not limited to, chemically bonded (e.g., covalently or ionically), biologically bonded, biochemically bonded, and/or otherwise associated with the electroactive supramolecular polymeric assembly. In an embodiment, being bound can include, but is not limited to, a covalent bond, a non-covalent bond, an ionic bond, a chelated bond, as well as being bound through interactions such as, but not limited to, hydrophobic interactions, hydrophilic interactions, charge-charge interactions, π-π stacking interactions, combinations thereof, and like interactions. In an embodiment in which the agent is a cell, cell-biomaterial interactions could be controlled through the inclusion of cell-adhesive peptides (e.g., RGD, YIGSR, KQAGDV, KHIFSDDSSE, KRSR), and protease-labile domains (e.g., APGL, VRN, or indeed oligoalanines such as those in the backbone of MTT1 and MTT2 that are degraded by elastase).

In an embodiment, the electroactive supramolecular polymeric assembly can be disposed onto a surface to form a film or layer on the surface. In an embodiment, the electroactive supramolecular polymeric assembly can be included in a pharmaceutical formulation. In an embodiment, the electroactive supramolecular polymeric assembly can be administered to the subject in need (e.g., a human patient) in an amount so as to provide a therapeutically effective amount of the agent.

In an embodiment, the electroactive supramolecular polymeric assemblies can be designed to control the release profiles and/or cell-biomaterial interactions by tuning the length of the electroactive oligoaniline, the ratio of electroactive to non-electroactive peptide blocks, the identity of the non-electroactive peptide (i.e., composition and sequence of amino acids), and the like. In a particular embodiment, increasing the length of the oligoalanine segments can render the electroactive supramolecular polymeric assembly more conductive and electrochemically stable (i.e., less likely to be spontaneously de-doped in biological milieu). In addition, electroactive supramolecular polymeric assemblies having a higher ratio of electroactive to non-electroactive peptide blocks can be more conductive. Furthermore, an embodiment in which a charged amino acid(s) is present in the electroactive supramolecular polymeric assembly can facilitate the inclusion of cationic drugs (e.g., antibacterials and antiarrhythmics).

As described herein, embodiments of the present disclosure provide for a method of delivering one or more agents. An embodiment of the method includes providing an electroactive supramolecular polymeric assembly (e.g., an electroactive ABA block copolymer) including the agent to a subject having a condition (e.g., a disease, an infection, an injury, a syndrome, a disability, a disorder, and a combination thereof). The electroactive supramolecular polymeric assembly can be administered in one or more ways as is best suited for the particular situation. Subsequently, an electrical stimulus can be used to activate electroactive supramolecular polymeric assembly. In particular, the electronic stimulus can be directed to an area where the agent is needed. For example, if the condition is pain or an infection at a particular location, the electronic stimulus can be directed to that area. In this way, the electrical stimulus causes the agent to be released from the electroactive supramolecular polymeric assembly at or near the location (e.g., specific area of the patient) of the condition. In an embodiment, the electrical stimulus can be periodically pulsed. In an embodiment, the electrical stimulus can be given at certain times of the day.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

Example

This Example discusses the preparation and characterization of films of electroactive supramolecular polymers based on non-electroactive oligoalanines and electroactive oligoanilines. Fibroblasts adhered to and proliferated on the films, and the delivery of the clinically relevant anti-inflammatory drug dexamethasone phosphate could be enhanced upon the application of an electrical stimulus.

Technologies that enable precise control of the amount of drugs in the blood stream or specific tissues facilitate the maintenance of the amount of drug within the therapeutic window, and controlling the chronopharmacology of a drug is particularly useful for the treatment of diseases with specific chronobiologies (e.g., cancers, infectious diseases, pain).[1-3] Drug delivery systems that respond to chemical (e.g., enzymes, pH) or physical (e.g.

electric/magnetic fields, light, pH, temperature) stimuli are potentially applicable for the treatment of such conditions.[2,3] Here we report the application of electroactive polymers (EAPs) that allow drug delivery enhanced by the application of an electrical stimulus.

Figure 1:
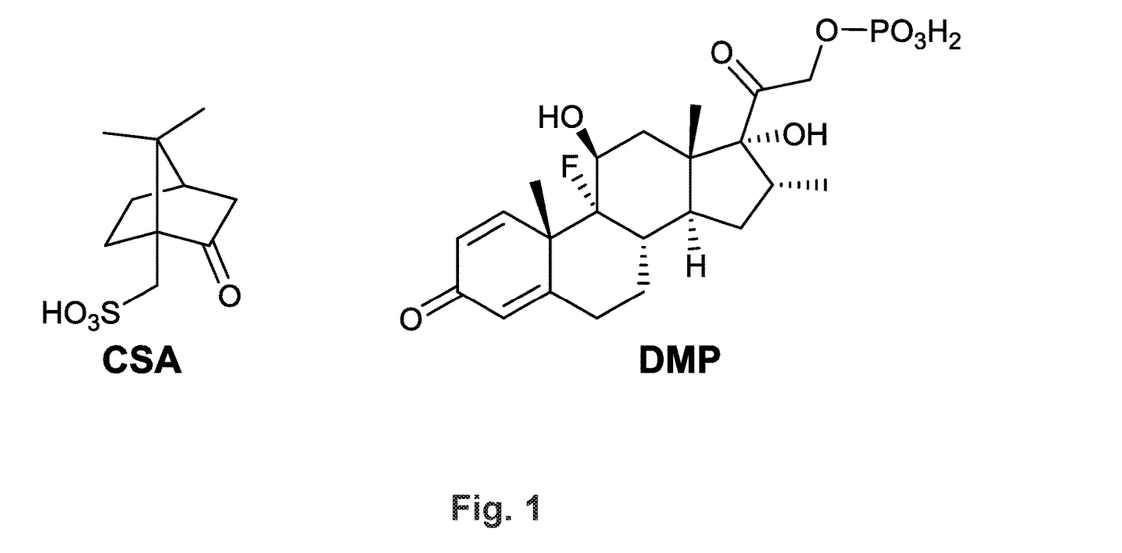
FIG. 1 illustrates camphorsulfonic acid (CSA) and dexamethasone phosphate (DMP).

EAPs have interesting electronic and optical properties and are currently investigated for use in electronic[4] and biomedical[5-8] industries. Polyaniline, polypyrrole and polythiophene derivatives are the EAPs most commonly investigated for biomedical applications.[9,10] In recent years block copolymers incorporating electroactive blocks (frequently oligoaniline-based polymers doped with camphorsulfonic acid, CSA, FIG. 1) have been investigated for use as electroactive tissue scaffolds capable of the electrical stimulation of the cells inhabiting them,[11] and as materials for electrochemically-triggered drug delivery.[12]

Polyaniline- and polypyrrole-based systems have been used to deliver a variety of drugs, including; adenosine triphosphate, dexamethasone phosphate (DMP, FIG. 1), DNA, dopamine, nerve growth factor and N-methylphenothiazine, as discussed in greater depth in reviews by Garg and co-workers[13] and Ndesendo and co-workers.[14] Here we report the application of electroactive molecular tongue-twisters (MTTs) based on electroactive oligoanilines and non-electroactive oligoalanines (i.e., oligoalanine-oligoaniline-oligoalanine) for the delivery of dexamethasone phosphate. The MTTs are solution processable and assemble into hierarchically structured supramolecular polymers[15-21] because of hydrogen bonding interactions between the oligoalanines in the solid state. Such supramolecular polymers have prospects for the preparation of conformal electroactive coatings for implantable biomaterials.

The electrochemically responsive blocks of oligoaniline were terminated with amines which enabled the initiation of ring-opening polymerization of α-amino acid N-carboxyanhydrides,[22] in this case alanine N-carboxyanhydride (Ala-NCA). The oligoanilines (tetraaniline and hexaaniline) were prepared using the methodology described in the literature (Scheme 2),[23,24] as was Ala-NCA (Scheme 3),[25] and they were polymerized at room temperature in anhydrous DMF, precipitated in diethyl ether and dried under vacuum (Scheme 1). The hexafluoroisopropanol (HFIP)-soluble fraction was extracted and dried under vacuum, yielding off-white solids that were used without further purification; tetraaniline-based molecular tongue-twister 1 (MTT1, oligoalanine-tetraaniline-oligoalanine) and hexaaniline-based molecular tongue-twister 2 (MTT2, oligoalanine-hexaaniline-oligoalanine), that are depicted in Scheme 1.

Scheme 1: Synthesis of molecular tongue-twisters (oligoalanine-oligoaniline-oligoalanine) from alanine N-carboxyanhydrides and amine-terminated oligoanilines. a) DMF, Ar, 96 h. For tetraaniline-based MTT1, n = 4, and m + p ≈ 10; whereas for hexaaniline-based MTT2, n = 6, and m + p ≈ 26.

Scheme 2 Synthesis of oligoanilines.

Scheme 3 Synthesis of alanine-N-carboxyanhydride.
A) α-pinene, EtOAc, 90° C., 4h.

The success of the polymerizations was confirmed spectroscopically. The presence of characteristic peaks in the IR spectra (FIGS. 5A-D) for amides and oligoanilines (shoulders at ca. 1541 cm$^{-1}$ (C=N and C=C stretches) and 1496 cm$^{-1}$ (C—C stretching))[26] NMR in deuterated HFIP suggested that MTT1 incorporated ca. 10 alanine units per tetraaniline (in line with the synthesis), whereas MTT2 incorporated 26 alanine units per hexaaniline, suggesting that polymers based on the less soluble hexaaniline required a greater number of alanines for the resulting polymer to be soluble. Yet their low solubility hampered determination of the molecular weight distributions via standard techniques such as GPC/SEC, light scattering or MALDI-TOF mass spectrometry.

Casting dilute solutions of the MTTs in HFIP allowed the preparation of water insoluble films of a few μm in thickness with μm scale roughness (Ra) or root mean square roughness (Rq) as determined by profilometry (Table 1). Undoped films were blue, whereas films doped with CSA (10 wt %) were green.

IR spectra of the films recorded in attenuated total reflectance (ATR) mode revealed subtle differences in the hierarchical supramolecular assembly of the polymers, with evidence of both α-helices and β-sheets in all spectra (FIGS. 5A-D),[27-29] with the α-helices induced by HFIP and the intermolecular β-sheets being partially responsible for the insolubility of the polymers in water (also observed in oligoalanine-rich proteins).[30-32] The oligoalanine blocks in undoped films of MTT1 assembled into both α-helices (amide I, 1649 cm$^{-1}$) and β-sheets (amide I, 1692 cm$^{-1}$; amide II, 1530 and 1517 cm$^{-1}$). Doping MTT1 with CSA altered the assembly of the MTTs, yet both α-helices (amide I, 1649 cm$^{-1}$; amide II, 1543 cm$^{-1}$) and β-sheets (amide I, 1690 cm$^{-1}$; amide II, 1530 and 1514 cm$^{-1}$) were present, although the β-sheet content was clearly reduced. The oligoalanine blocks in undoped films of MTT2 were predominantly amorphous (amide I, 1646 cm$^{-1}$; amide II, 1533 cm$^{-1}$) with some β-sheets (amide I, 1629 cm$^{-1}$; amide II, 1518 cm$^{-1}$). Doping MTT2 with CSA reduced the β-sheet content (weak amide I, 1690 cm$^{-1}$; weak amide II, 1530 and 1514 cm$^{-1}$), and the chains were predominantly amorphous (amide I, 1646 cm$^{-1}$; amide II, 1535 cm$^{-1}$)[27-29]

Wide angle XRD patterns for the films (FIGS. 6A-D) supported the results from IR spectroscopy, which showed evidence of both α-helices (broad peak at 2θ=19.4o, d-spacing 4.58 Å) and β-sheets (broad peak at 2θ=16.7° and 19.9°, d-spacings of 5.31 and 4.46 Å, respectively) also observed in oligoalanine-rich proteins.[29] Films composed of MTT1 showed some peaks reported for tetraniline-based supramolecular polymers (peaks at 2θ=11.7°, 19.5°, 20.3°, 20.7° and 29.7°, d-spacings of 7.56, 4.55, 4.37, 4.29 and 3.01 Å, respectively),[33] and were clearly more crystalline (higher Xc) than those of CSA-doped MTT1 (FIGS. 6A-D and Table 1) because the presence of the bulky CSA anions interfered with the assembly of the oligoaniline blocks.[12,34] Films of MTT2 were amorphous in both the undoped or CSA-doped state.

The conductance of films of the MTTs were measured as previously reported.[12] Undoped films of tetraaniline-based MTT1 had a conductivity of ca. 1.6×10$^{-8}$ S cm$^{-1}$, that was moderately increased by doping with CSA to ca. 2.5×10$^{-8}$ S cm$^{-1}$ (Table 1). Undoped films of hexaaniline-based MTT2 had a conductivity of ca. 7.3×10$^{-8}$ S cm$^{-1}$, that was moderately increased by doping with CSA to ca. 8.6×10$^{-8}$ S cm$^{-1}$ (Table 1). The higher conductivity of MTT2-based films was because of the greater level of conjugation in the backbone of hexaaniline than in tetraaniline. These conductivities are lower than those of mammalian tissues (typically ≥10$^{-4}$ S cm$^{-1}$)[35-37] that should enable the controlled delivery of a drug upon the application of an electrical potential to the EAPs.

We studied the release profiles of the anti-inflammatory drug DMP from MTT films into phosphate buffered saline

TABLE 1

Surface and physicochemical properties of the polymer films

|  | $R_a$ (μm) | $R_q$ (μm) | $X_c$ (%) | Conductivity, σ (S cm$^{-1}$) |
|---|---|---|---|---|
| Glass substrate | 0.730 ± 0.153 | 0.905 ± 0.182 | N/A[a,b] | N/A |
| MTT1 undoped | 0.760 ± 0.299 | 3.272 ± 6.352 | 68.2[a] | 1.59 × 10$^{-8}$ ± 28% |
| MTT1 doped with CSA | 0.760 ± 0.516 | 1.020 ± 0.637 | 30.1[a] | 2.49 × 10$^{-8}$ ± 33% |
| MTT2 undoped | 0.700 ± 0.018 | 0.085 ± 0.024 | 0.0[a] | 7.32 × 10$^{-8}$ ± 32% |
| MTT2 doped with CSA | 0.475 ± 0.009 | 0.060 ± 0.014 | 0.0[a] | 8.55 × 10$^{-8}$ ± 32% |

[a]As determined by XRD.
[b]Not applicable.

Figure 7:
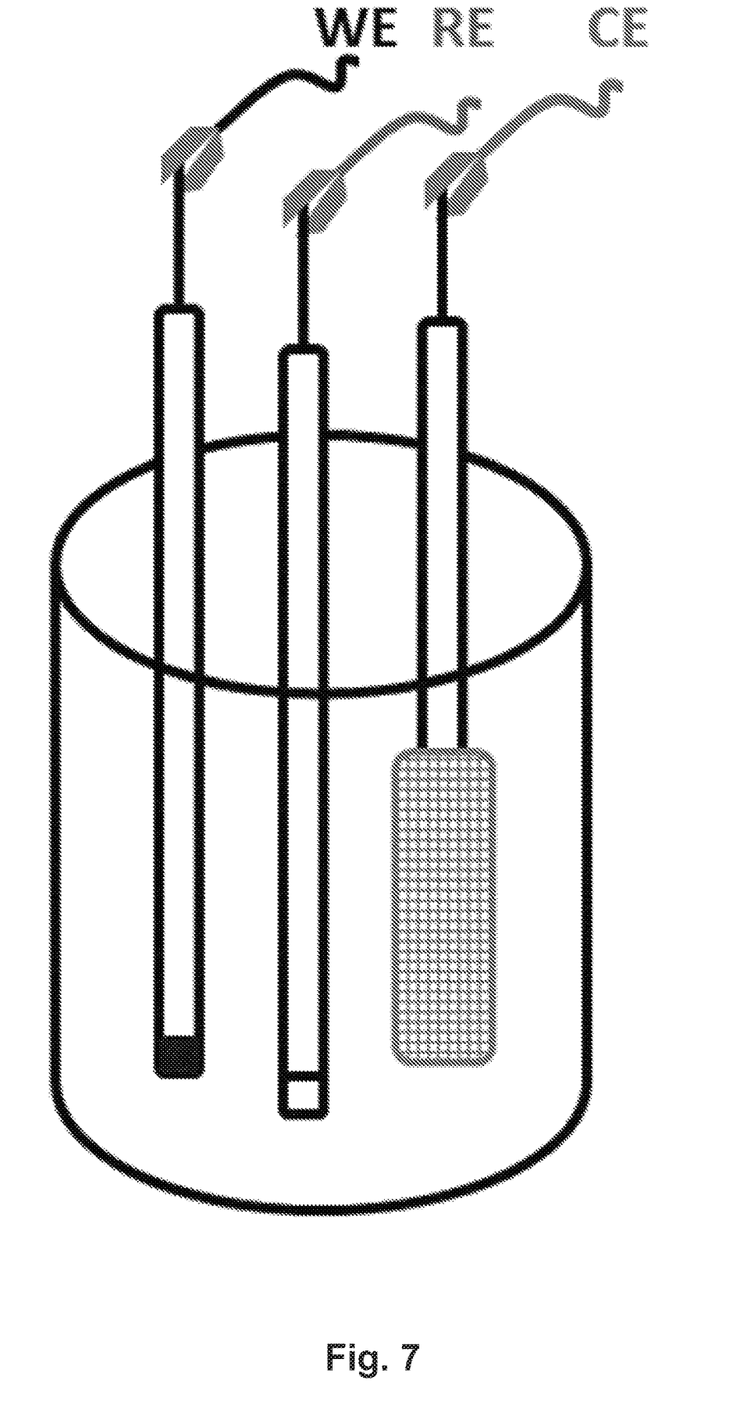
FIG. 7 is a schematic of an experimental setup for electrochemically-triggered drug delivery. Pt mesh counter electrode (CE), Ag/AgCl reference electrode (RE), DMP-doped polymer film coated on a glass carbon working electrode (WE).
Figure 8A:
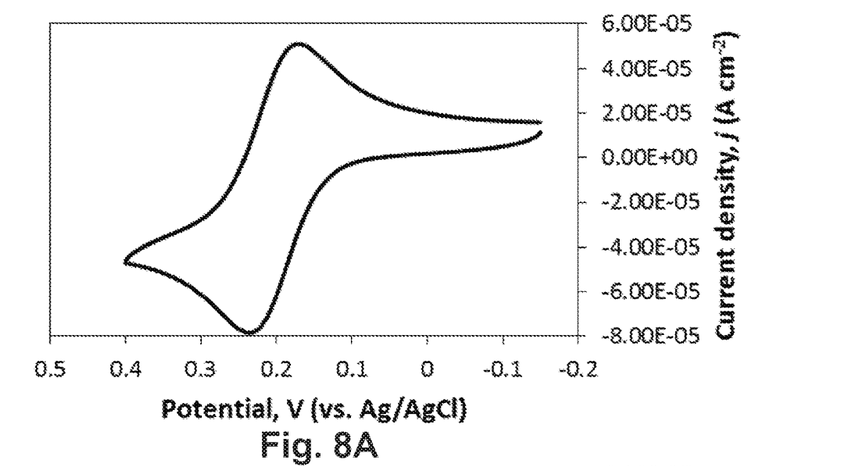
Figure 8B:
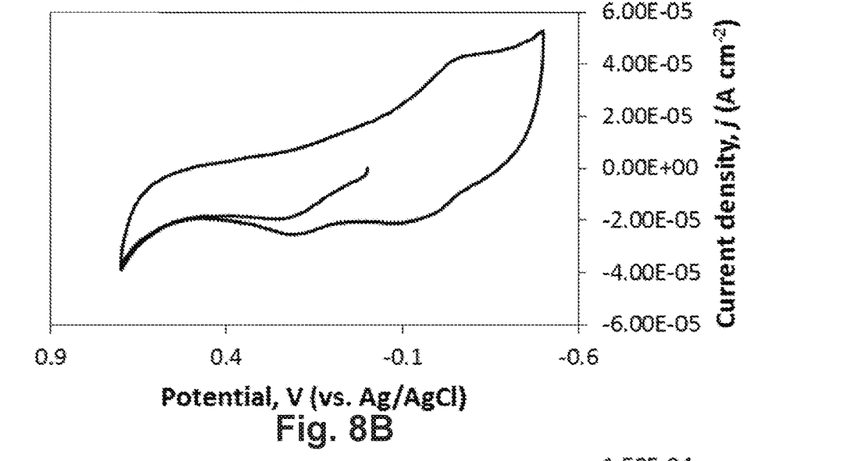
FIG. 8B is a voltammogram of DMP-doped MTT1. Scan rate=50 mV $s^{-1}$.
Figure 8C:
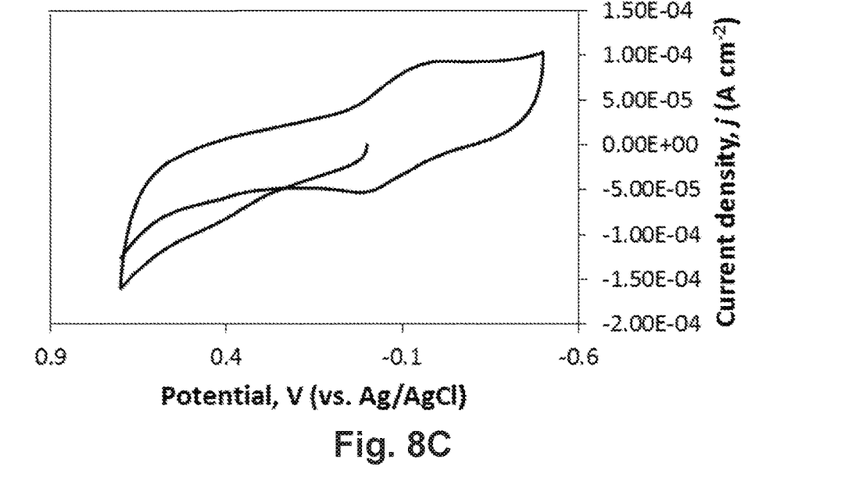
FIG. 8C is a voltammogram of DMP-doped MTT2. Scan rate=50 mV $s^{-1}$.

(PBS) in the absence or presence of an electrical stimulus using the experimental setup depicted in FIG. 7. Cyclic voltammograms (FIGS. 8A-C) of the DMP-doped films of MTT1 presented a redox process at ca. 0.26 V (leucoemeraldine to emeraldine 1 transition), whereas those for MTT2 presented a process at 0.42 V (emeraldine 1 to emeraldine 2 transition), confirming the greater conjugation in the backbone of the longer oligomers (potentials are reported vs. a Ag/AgCl reference electrode calibrated with ferrocenemethanol).

Figure 2:
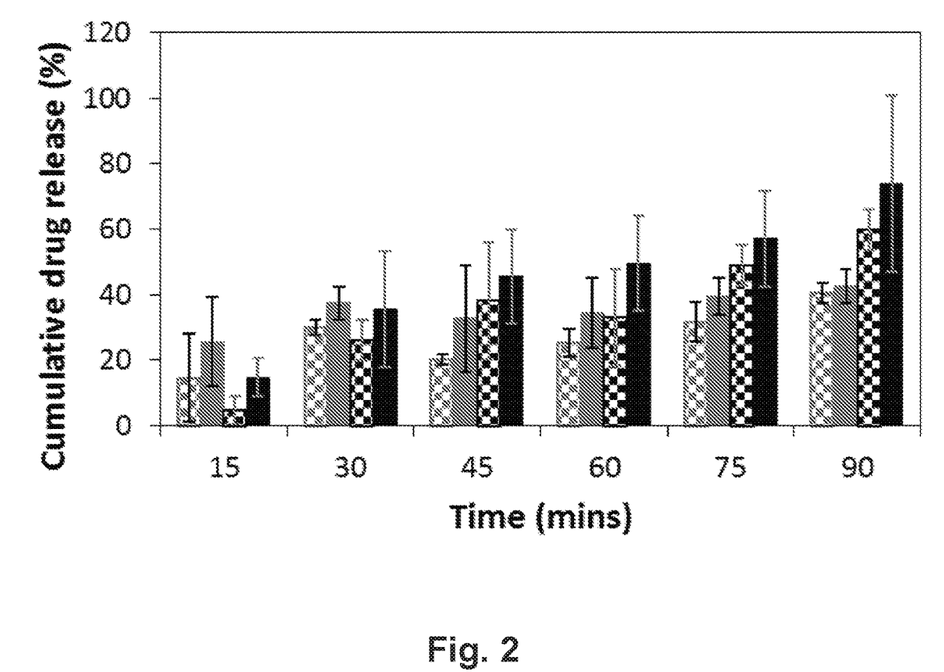
FIG. 2 shows DMP release from films of MTT1 and MTT2 in the absence and presence of electrical stimulation as determined by UV spectroscopy. MTT1 without electrical stimulation is illustrated with checked grey bars; MTT1 with electrical stimulation solid grey bars; MTT2 without electrical is illustrated with stimulation checked black bars; MTT2 with electrical stimulation is illustrated with solid black bars.

We monitored the release of DMP at specific time points spectroscopically, using its characteristic UV absorption at 242 nm. DMP loadings in the films were at 10 wt %. Passive release from films of MTT1 (FIG. 2, grey checked bars) and MTT2 (FIG. 2, black checked bars) was observed, however, release was moderately enhanced by the application of an electrical stimulus (FIG. 2; MTT1 grey bars, MTT2 black bars), typically by 10 to 20% for the first five rounds of stimulation, after which the profiles for MTT1 in the absence/presence of stimulation was observed to be equal which suggests that it is more prone to spontaneous de-doping than the more highly conjugated MTT2. We believe that the release profiles could be improved by tuning both the length of the electroactive oligoaniline, the ratio of electroactive to non-electroactive peptide blocks, and the identity of the non-electroactive peptide (i.e. composition and sequence of amino acids).

Figure 3A:
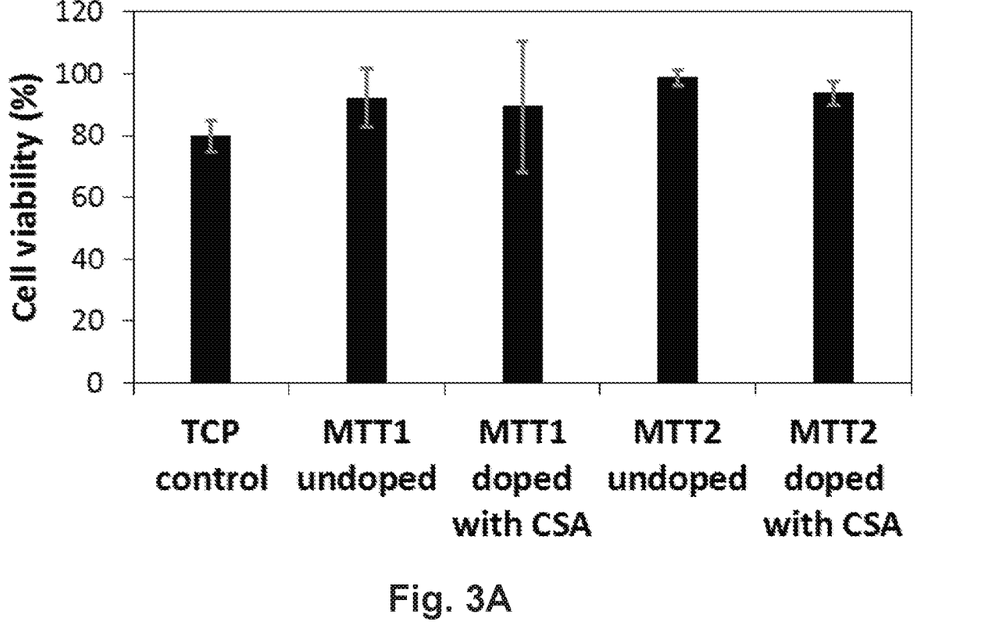
FIG. 3A is a graph of assessment of the cell viability of human dermal fibroblasts on various surfaces after 2 days in culture as determined using a LIVE/DEAD® Viability/Cytotoxicity Kit.
Figure 3B:
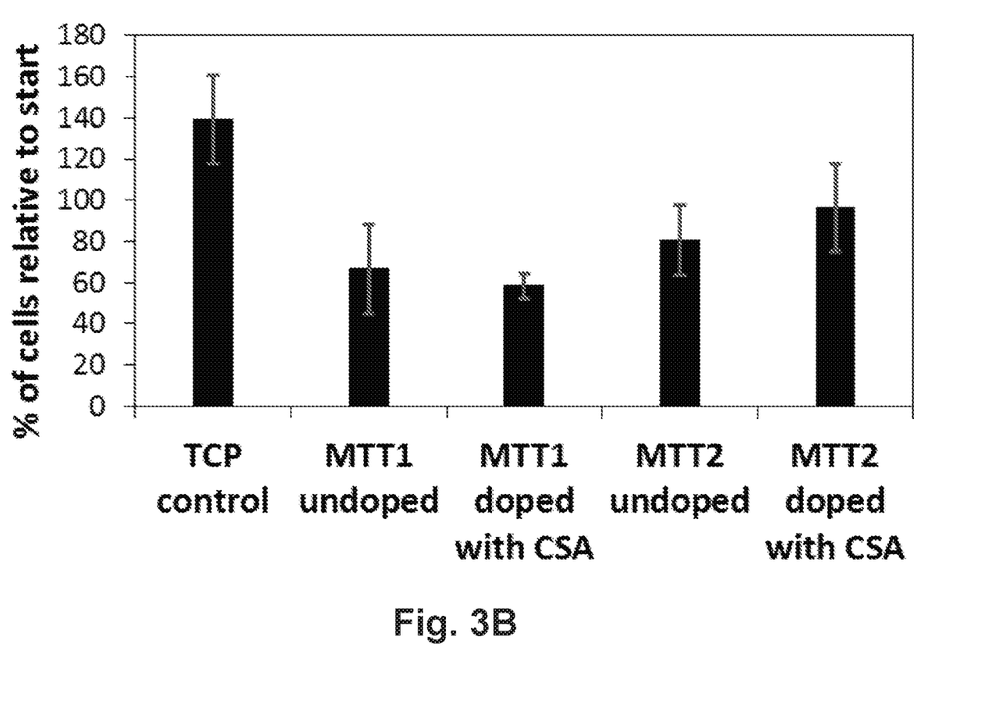
FIG. 3B is a graph of assessment of cell adhesion on various surfaces after 2 days as determined by the AlamarBlue® assay.
Figure 4A:
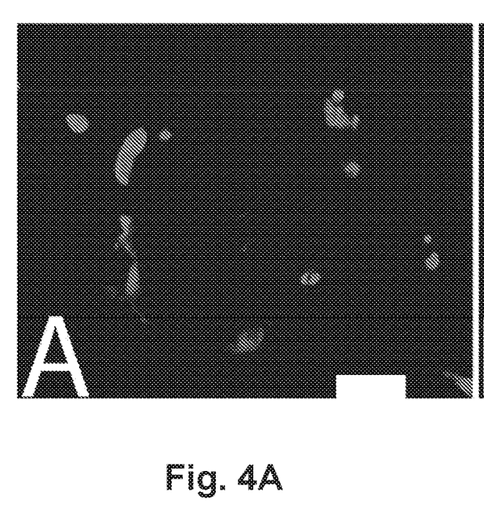
Figure 4B:
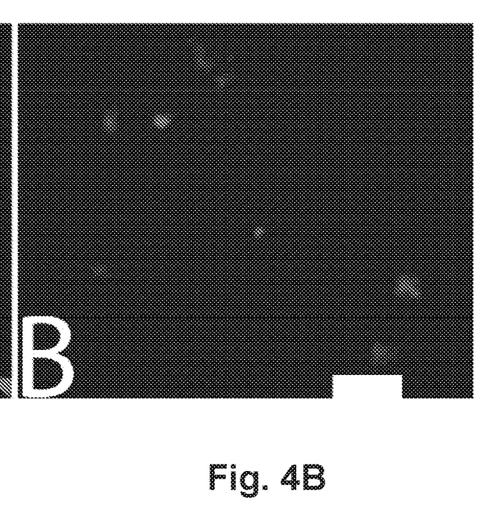
Figure 4C:
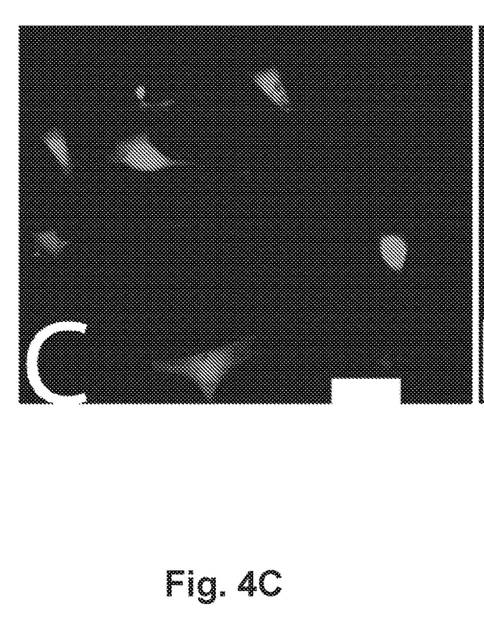
Figure 4D:
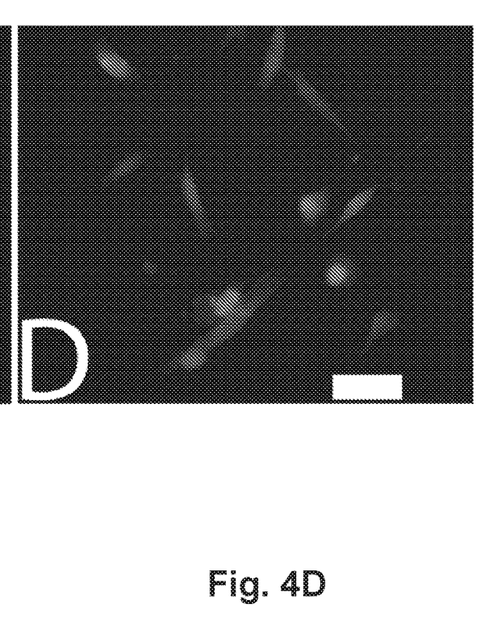
Figure 5A:
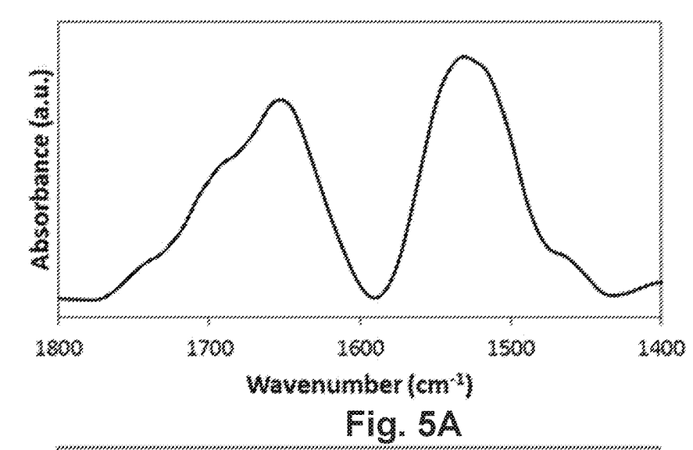
Figure 5B:
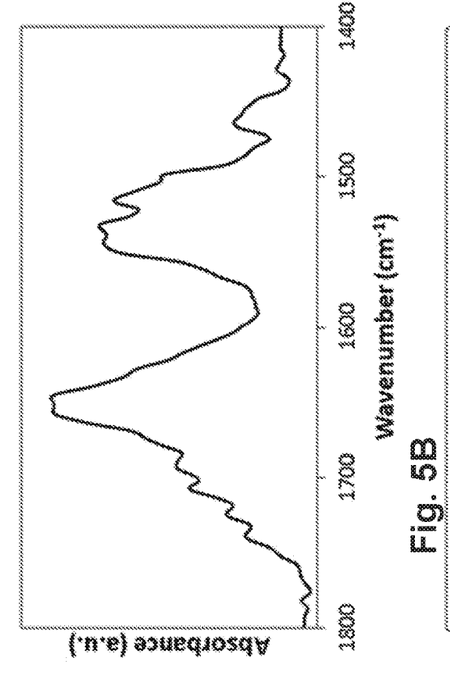
Figure 5C:
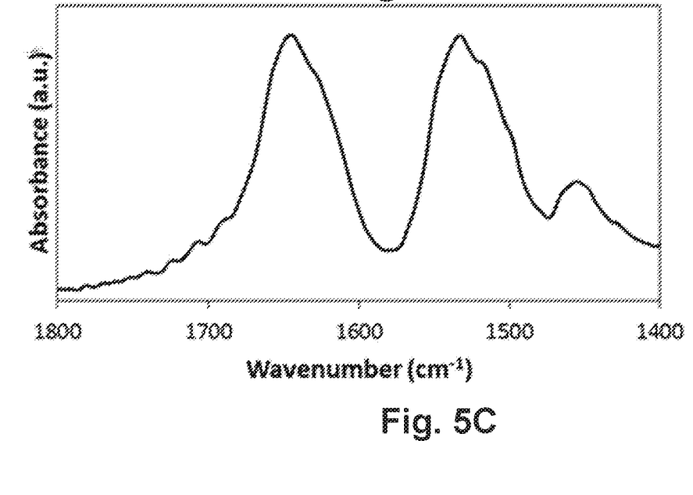
Figure 5D:
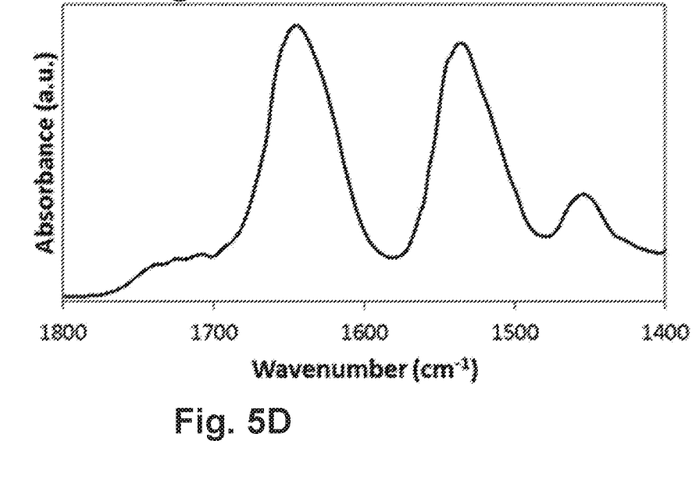
Figure 6A:
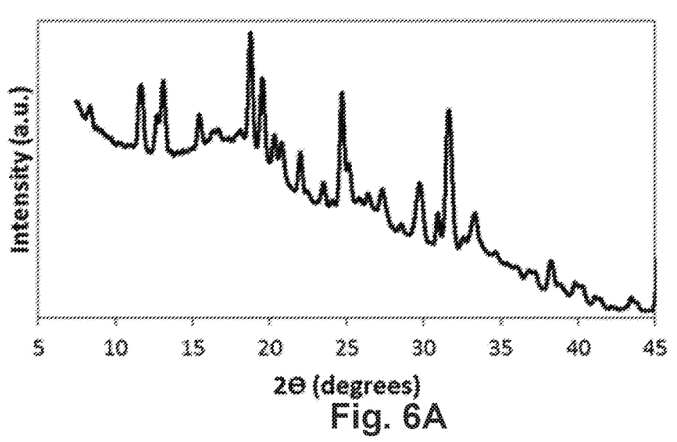
Figure 6B:
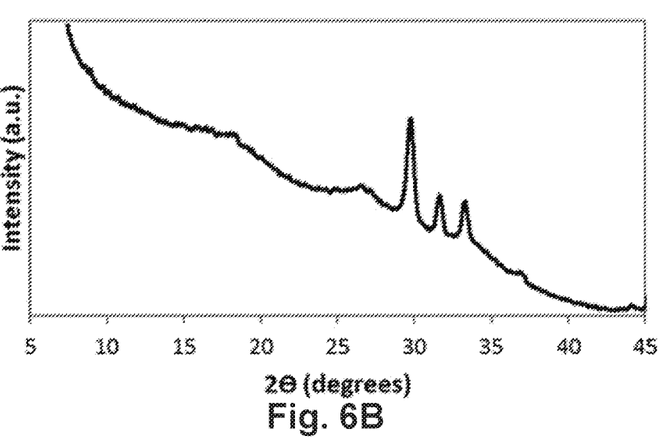
Figure 6C:
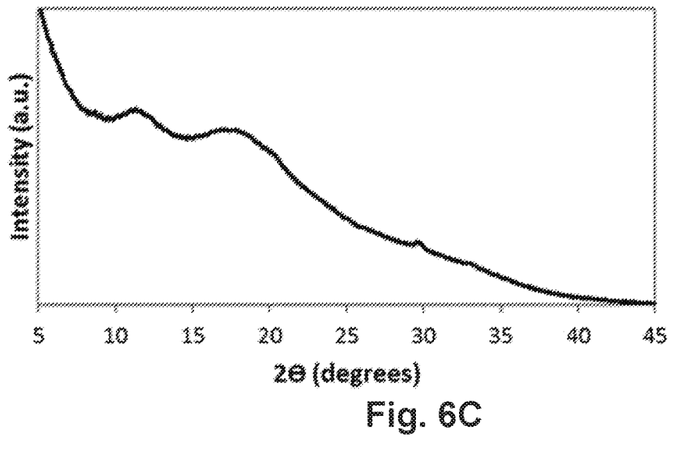
Figure 6D:
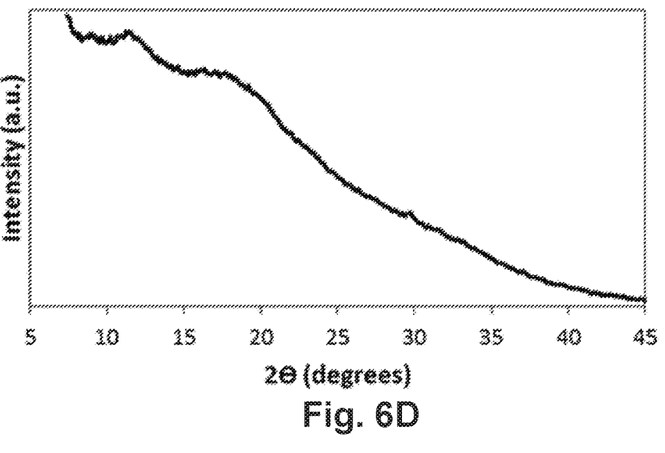
Figure 9:
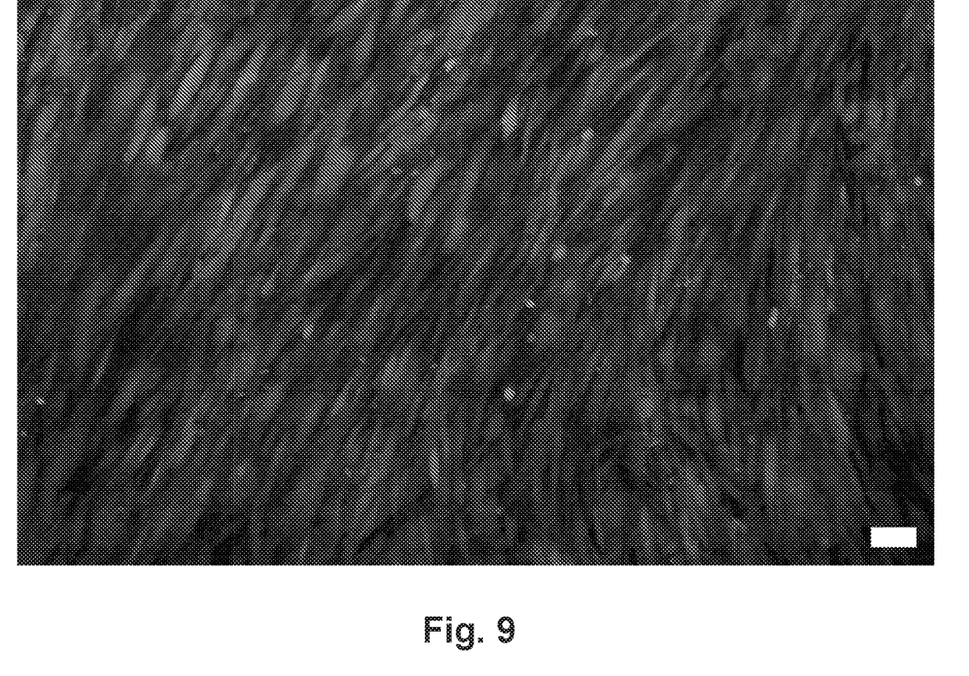
FIG. 9 shows HDF adhesion on the surface of Corning Costar® Tissue Culture Plates (TCP control). Live cells were stained green by calcein and dead cells were stained red by ethidium using a LIVE/DEAD® Viability/Cytotoxicity Kit. The scale bar represents 100 µm.

Analogous electroactive block copolymers incorporating CSA-doped oligoalanines have been shown to support the adhesion of a variety of cells including fibroblasts, keratinocytes, osteoblasts, PC12 cells and Schwann cells.[11] We found that cell viability for the HDFs cultured on the films of MTTs was comparable, and indeed somewhat better than TCP controls (FIG. 3A). However, the adhesion of human dermal fibroblasts (HDFs) to films of undoped or CSA-doped $MTT_1$ was poor by comparison with commercially available Corning Costar® tissue culture plate (TCP) controls as determined using the AlamarBlue® assay (FIG. 3B), and cells had relatively rounded morphologies indicative of poor cell adhesion (FIGS. 4A and 4B), particularly by comparison with TCP controls (FIG. 9). Interestingly, HDF adhesion to films of undoped or CSA-doped MTT2 was moderately better, with cells more likely to adopt a spread morphology (FIGS. 4C and 4D). For certain applications, non cell-adhesive biomaterials are interesting candidates, such as for the manufacture of anti-adhesion membranes;[38] however, for other applications (e.g. tissue scaffolds) cell adhesion is beneficial. We believe that cell adhesion could be improved by incorporating cell adhesive peptides (e.g., the ubiquitous RGD)[10,16,39-41] in the backbone of such EAPs.

EXPERIMENTAL

Materials and Synthetic/Analytical Methods

Unless otherwise stated, all chemicals were of ACS grade, purchased from Sigma-Aldrich and used as received without further purification. $^1$H and $^{13}$C NMR spectra were recorded on an Agilent 600 MHz NMR spectrometer, using residual solvent $^1$H peaks as internal references for the $^1$H NMR spectra and the solvent $^{13}$C peaks as references for the $^{13}$C NMR spectra. The following notation is used for the $^1$H NMR spectral splitting patterns: multiplet (m), broad (br). Infrared spectroscopy was carried out on a Thermo Scientific Nicolet 380 FT-IR Spectrometer (Thermo Fisher Scientific Inc., USA). Spectra were recorded in ATR mode at 21° C., with a 1 $cm^{-1}$ resolution and 64 scans (corrected for background and atmosphere using OMNIC software provided with the spectrometer).

SYNTHESIS OF NITRO-TERMINATED ANILINE TETRAMERS ($O_2N$-$A_{N4}$-$NO_2$)

The synthesis of the nitro-terminated aniline tetramers was carried out in accordance with the literature and analytical data were in agreement with the literature (Scheme 2).[23,24]

SYNTHESIS OF AMINE-TERMINATED ANILINE TETRAMERS ($H_2N$-$A_{N4}$-$NH_2$)

The synthesis of the amine-terminated aniline tetramers was carried out in accordance with the literature and analytical data were in agreement with the literature (Scheme 2).[23,24] SYNTHESIS OF NITRO-TERMINATED ANILINE HEXAMERS ($O_2N$-$A_{N6}$-$NO_2$)

The synthesis of the nitro-terminated aniline hexamers was carried out in accordance with the literature and analytical data were in agreement with the literature (Scheme 2).[23,24]

SYNTHESIS OF AMINE-TERMINATED ANILINE HEXAMERS ($H_2N$-$A_{N6}$-$NH_2$)

The synthesis of the amine-terminated aniline hexamers was carried out in accordance with the literature and analytical data were in agreement with the literature (Scheme 2).[23,24]

SYNTHESIS OF L-ALANINE N-CARBOXYANHYDRIDE (ALA-NCA)

The synthesis of the L-alanine N-carboxyanhydride was carried out in accordance with the literature and analytical data were in agreement with the literature (Scheme 3).[25]

SYNTHESIS OF TETRAANILINE-BASED MOLECULAR TONGUE TWISTER 1 (MTT1)

MTT1 was synthesised by adaption of the literature methodology.[22,25] 1 molar eq. of amine-terminated aniline tetramer ($H_2N$-$A_{N4}$-$NH_2$) and 10 molar eq. L-alanine N-carboxyanhydride (ALA-NCA) were stirred in anhydrous DMF (solids at 100 mg $mL^{-1}$) at room temperature under an inert atmosphere of argon for 4 days. The product was precipitated in diethyl ether, the solids isolated by filtration, washed with diethyl ether and dried under high vacuum for 48 hours. The solids were suspended in hexafluoroisopropanol (HFIP) and the HFIP-soluble fraction was extracted by shaking the suspension in 15 mL of HFIP at 1000 rpm for 24 hours, after which the solids were removed by filtration and the product isolated by evaporation of the HFIP with a rotary evaporator, followed by drying under high vacuum for 48 hours (Scheme 1). MTT1 was isolated in a yield of 10 mass %, relative to the total mass of starting materials (ALA-NCA and $H_2N$-$A_{N4}$-$NH_2$). 1H NMR (600 MHz, HFIP-d2): δH=7.57-6.58 (br m, 16H, Ar—H), 4.14 (br m, 10H, CHCH3), 1.37 (br m, 30H, CH3). IR (ATR) vmax $cm^{-1}$ 1648 (C=O, amide 1), 1560 (C=N and C=C stretch, oligoaniline), 1530 (C=O, amide 2), 1496 (C—C stretch, oligoaniline).

SYNTHESIS OF HEXAANILINE-BASED MOLECULAR TONGUE TWISTER 2

MTT2 was synthesised by adaption of the literature methodology.[22,25] 1 molar eq. of amine-terminated aniline hexamer ($H_2N$-$A_{N6}$-$NH_2$) and 10 molar eq. L-alanine N-carboxyanhydride (ALA-NCA) were stirred in anhydrous DMF (solids at 100 mg mL$^{-1}$) at room temperature under an inert atmosphere of argon for 4 days. The product was precipitated in diethyl ether, the solids isolated by filtration, washed with diethyl ether and dried under high vacuum for 48 hours. The solids were suspended in hexafluoroisopropanol (HFIP) and the HFIP-soluble fraction was extracted by shaking the suspension in 15 mL of HFIP at 1000 rpm for 24 hours, after which the solids were removed by filtration and the product isolated by evaporation of the HFIP with a rotary evaporator, followed by drying under high vacuum for 48 hours (Scheme 1). MTT2 was isolated in a yield of 9 mass %, relative to the total mass of solids (ALA-NCA and $H_2N$-$A_{N6}$-$NH_2$). 1H NMR (600 MHz, HFIP-d2): δH=7.57-6.58 (br m, 24H, Ar—H), 4.14 (br m, 26H, CHCH$_3$), 1.31 (br m, 78H, CH$_3$). IR (ATR) vmax cm$^{-1}$ 1644 (C=O, amide 1), 1560 (C=N and C=C stretch, oligoaniline), 1532 (C=O, amide 2), 1496 (C—C stretch, oligoaniline).

Film Preparation and Characterization

Film Preparation

Films were prepared by casting solutions of the copolymers in hexafluoroisopropanol (HFIP, typically 0.05 g/mL) onto HFIP insoluble substrates, (e.g., microscope slides with dimensions of 2.5 cm×5 cm or glassy carbon electrodes with surface areas of 0.0314 cm$^2$). The solvent was allowed to evaporate in a fume hood, and the films were subsequently dried under vacuum for 48 hours at room temperature. The polymers were doped with camphorsulfonic acid (CSA) by the addition of CSA to the HFIP solution prior to casting on microscope slides. Unless otherwise stated CSA doping was at a mass ratio of 1:10 CSA:MTT.

Profilometry

Profilometry was carried out using a Veeco Dektak 150 Stylus Profilometer (Veeco Instruments Inc., NY) fitted with a diamond stylus tip. The profilometer was isolated on an air table to reduce ambient vibrations. The profilometer was operated at 10 mg of stylus force, and used to record profiles of distances of ca. 1 cm, recording data points every 555 nm. Data analysis was carried out with the software provided by the manufacturer, which allowed the determination of the thickness and roughness of the films. The surface roughness parameters are analyzed and reported in accordance with the ISO 25178 series. The average roughness (Ra) is the arithmetic average of the deviation from the mean line, and is the most used international parameter of roughness, and the root-mean-square roughness (Rq) is based upon this.

Conductivity Determination

The conductance of films of the polymers were measured in accordance with protocol IPC-TM-650, number 2.5.17.2 described by the Institute for Interconnecting and Packaging Electronic Circuits. Films supported on glass slides were examined by chronoamperometry using a CHI900C electrochemical workstation (CHI instruments, Austin, Tex.). Chronoamperometric measurements were made with a two-point probe system (copper alligator clips), by connecting counter and reference electrodes together. Briefly, two thin strips of adhesive-backed copper tape (Ted Pella, Inc., Redding, Calif.) were attached to the films, parallel to one another, separated by a distance of 0.5 cm. The working and counter electrodes were clipped on the strips of copper tape, and the current measured for 50 seconds during a potential step experiment at 10 V. The electrodes were moved to different positions after each measurement, and the current passed was recorded in at least five different positions. The resistance (R, Ω) of the films was determined in accordance with equation 1:

$$R=V/I \qquad (1)$$

The resistivity (Ω/cm) of the films was determined in accordance with equation 2:

$$\rho=Rwt/L \qquad (2)$$

In which: w corresponds to the width of the film in cm (2.5 cm); t corresponds to the thickness of the film in cm (as determined via profilometry); and L corresponds to the length of the film in cm (0.5 cm). The conductivity (S/cm) of the films was determined in accordance with equation 3:

$$\sigma=1/\rho \qquad (3)$$

X-Ray Diffraction (XRD)

XRD data was collected on a Rigaku R-Axis Spider diffractometer with an image plate detector using a graphite monochromator with CuKα radiation (λ=1.5418 Å) at room temperature. The instrument was controlled using Rapid/XRD diffractometer control software (Rapid/XRD Version 2.3.8., Rigaku Americas Corporation, The Woodlands, Tex.). The integration of the two dimensional data into a one dimensional pattern was accomplished using 2DP (2DP Version 1.0., Rigaku Americas Corporation, The Woodlands, Tex.). Percentage crystallinities were determined by taking the ratio of the crystalline area to the amorphous area in the XRD spectrum.

In Vitro Drug Delivery and Cell Culture Studies

Preparation of Drug Doped Films

Films of ca. 3-4 mg were prepared by casting solutions of the polymers and DMP (at a mass ratio of 10:1 polymer:DMP) in hexafluoroisopropanol (typically 0.05 g/mL) onto a glassy carbon electrode (0.0314 cm$^2$, CH Instruments, Inc.). The solvent was allowed to evaporate in a fume hood, and the films were subsequently dried under vacuum for 48 hours at room temperature.

Drug Delivery Studies

Voltammetry experiments were carried out using a CHI6273C electrochemical analyzer (CH Instruments, Inc.). Phosphate buffered saline (PBS, pH 7.0) was deoxygenated for 10 minutes with argon before the electrochemical measurements were made. Electrochemically-triggered release (i.e., de-doping) of DMP from the films deposited on glassy carbon substrates by potential cycling, was achieved using a three-electrode system consisting of one polymer film-coated glassy carbon working electrode, a Pt mesh counter electrode, and an Ag/AgCl reference electrode in 4 mL PBS. Prior to each experiment there was a 10 s "quiet time", the initial potential was 0 V, the high potential was 0.7 V, the low potential was −0.5 V, the initial scan was positive, the current was measured at intervals of 0.001 V, the scan rate used in all experiments was 50 mV s$^{-1}$, and this stimulation lasted 62 seconds. The films were allowed to rest for 14 minutes after which the quantity of DMP in solution was quantified by UV spectroscopy. The medium was unchanged between cycles, and the data are reported as cumulative release as a percentage of the total mass of drug in the film over the period of the experiment. These data are compared to passive DMP release from unstimulated films measured every 15 minutes. DMP release was quantified by UV spectroscopy using a BioTek Epoch® plate reader (BioTek US, Winooski, Vt.) equipped with a Take3 Micro-volume Plate and Gen5 v2.04 Software supplied with the plate reader. Two samples of 2 μL were removed from the release medium at specific time points and absorbance readings were carried out at 242 nm (the characteristic absorbance band of DMP). Absorptions were corrected by subtracting the reading of PBS alone from each sample. A standard calibration curve for DMP was plotted to define the quantitative relationship between the observed absorbance and the concentration of DMP. Prior to the experiment, the mass of the drug-doped polymer film on the substrate was determined by subtracting the mass of the substrate from the mass of the polymer-coated substrate. Data are plotted as % DMP release relative to the quantity of DMP theoretically in the film at the beginning of the experiment, and all data are the average of at least three samples.

Cell Culture

All reagents were purchased from Invitrogen (Carlsbad, Calif.) unless otherwise noted. Human dermal fibroblasts (HDFs) were purchased from Lonza (Gaithersburg, Md.). Commercially available tissue-culture treated Corning® Costar® tissue culture plates were used for control experiments and sections of glass slides coated with polymer films of ca. 1 cm$^2$ (optionally doped with CSA) were inserted in tissue culture plates and sterilized by incubation in 70% ethanol solution, followed by exposure to UV for 30 minutes. After sterilization, films were incubated for 30 minutes under 3 mm of Dulbecco's Modified Eagle Medium (DMEM) supplemented with 10% fetal bovine serum, 100 U ml$^{-1}$ penicillin, 100 μg ml$^{-1}$ streptomycin, 0.25 μg ml$^{-1}$ amphotericin, 0.1 mM non-essential amino acids, and 1 ng ml$^{-1}$ basic fibroblast growth factor. Medium was aspirated and replaced prior to HDF seeding. Cell viability before starting the experiment was determined by the Trypan Blue (Sigma, USA) exclusion method, and the measured viability exceeded 95% in all cases. Cells were seeded on tissue-culture treated Corning® Costar® tissue culture plates at 10,000 cells per cm2, and all other substrates (i.e. MTT-based films) at 2,500 cells per cm$^2$, under 3 mm of medium, and incubated at 37° C., 95% humidity, and a $CO_2$ content of 5%. The cell adhesion and quantification studies were carried out using the AlamarBlue® assay in accordance with the manufacturers instructions. After 2 days the medium was aspirated and the films were washed gently with PBS, followed by the addition of fresh medium containing 10% v/v AlamarBlue® reagent. After 2.5 hours of culture, the medium was aspirated and replaced with fresh medium, and 100 μL of the aspirated medium containing the AlamarBlue® reagent was placed in a 96 well plate, and the fluorescence was measured with a fluorimeter (Synergy HT Multi-Mode Microplate Reader, Biotek US, Winooski, Vt.). Two controls were considered during the measurement of the fluorescence: the first was wells containing the medium alone (i.e. no cells of AlamarBlue® reagent), which was not fluorescent; and the second was wells that contained the AlamarBlue® reagent but no cells (used for background correction). Numbers of cells adhered to the various surfaces studied herein are reported relative to their initial seeding density, which was assigned an arbitrary value of 100%. After another 2 days (i.e. at 4 days after initial seeding) the viability of the cells was evaluated using a LIVE/DEAD® Viability/Cytotoxicity Kit for mammalian cells (Molecular Probes, Eugene, Oreg.). The medium was removed and the cells were incubated with 4 μM ethidium and 2 μM calcein AM in PBS for 15 min at 37° C. in the dark. Live cells were stained green because of the cytoplasmic esterase activity, which results in reduction of calcein AM into fluorescent calcein, and dead cells were stained red by ethidium, which enters into cells via damaged cell membranes and becomes integrated into the DNA strands. Fluorescence images of cells were captured using an Olympus DP80 camera (Olympus America Inc., Miami, Fla., USA) attached to a fluorescence microscope (IX-70; Olympus America Inc.) running CellSens 1.12 software (Olympus America Inc.). Cells were counted with ImageJ.

CONCLUSIONS

Herein we described electrically-triggered drug release from electroactive molecular tongue-twisters (i.e., oligoalanine-oligoaniline-oligoalanine). The electroactive ABA block copolymers based on A) non-electroactive oligoalanines, and B) electroactive blocks of oligoanilines, represents a novel platform for drug delivery. The physicochemical properties of the films were characterized by various techniques, and we found that hexaaniline-based MTT2 was more conductive and appeared to be more electrochemically stable towards de-doping than tetraaniline-based MTT1. While HDFs cultured on the surfaces of such films adhered weakly, this could be improved by incorporating cell-adhesive moieties.[39-41] While imperfect, such EAPs represent valuable lead structures for the development of materials that enable us to deliver drugs with clinically relevant chronopharmacologies, and facilitate the treatment of conditions with specific chronobiologies (e.g. infectious diseases, pain). We believe that it should be possible to rationally control the release profiles and cell-biomaterial interactions by tuning the length of the electroactive oligoaniline, the ratio of electroactive to non-electroactive peptide blocks, and the identity of the non-electroactive peptide (i.e. composition and sequence of amino acids). Specifically, increasing the length of the oligoalanine segments should render them more conductive and electrochemically stable (i.e. less likely to be spontaneously de-doped in biological milieu). The composition and sequence of amino acids in the non-electroactive peptide dictate the charge and hydrophobicity of the materials, which play roles in the self-assembly of the peptides (i.e., hydrogen bonding interactions, electrostatic interactions) and protein deposition on their surfaces which may be important for cell adhesion. Cell-biomaterial interactions could be controlled through the inclusion of cell-adhesive peptides (e.g., RGD, YIGSR, KQAGDV, KHIFSDDSSE, KRSR),[39-41] and protease-labile domains (APGL, VRN, or indeed oligoalanines such as those in the backbone of MTT1 and MTT2 that are degraded by elastase),[40] potentially facilitate their degradation in vivo. Furthermore, molecules with higher ratios of electroactive to non-electroactive peptide blocks should be more conductive, and the inclusion of charged amino acids may facilitate the inclusion of cationic drugs (antibacterials, antiarrhythmics, etc.).[42]

REFERENCES

A. S. Mandal, N. Biswas, K. M. Karim, A. Guha, S. Chatterjee, M. Behera and K. Kuotsu, J. Controlled Release, 2010, 147, 314.

B. Chertok, M. J. Webber, M. D. Succi and R. Langer, Mol. Pharm., 2013, 10, 3531.

M. E. Caldorera-Moore, W. B. Liechty and N. A. Peppas, Acc. Chem. Res., 2011, 44, 1061.

P. Leclere, M. Surin, P. Jonkheijm, O. Henze, A. P. H. J. Schenning, F. Biscarini, A. C. Grimsdale, W. J. Feast, E. W. Meijer, K. Mullen, J. L. Bredas and R. Lazzaroni, Eur. Polym. J., 2004, 40, 885.

M. Berggren and A. Richter-Dahlfors, Adv. Mater., 2007, 19, 3201.
Z. L. Yue, S. E. Moulton, M. Cook, S. O'Leary and G. G. Wallace, Adv. Drug Deliv. Rev., 2013, 65, 559.
A. Guiseppi-Elie, Biomaterials, 2010, 31, 2701.
J. Rivnay, R. M. Owens and G. G. Malliaras, Chem. Mater., 2014, 26, 679.
A. D. Bendrea, L. Cianga and I. Cianga, J. Biomater. Appl., 2011, 26, 3.
J. G. Hardy, J. Y. Lee and C. E. Schmidt, Curr. Opin. Biotechnol., 2013, 24, 847.
B. L. Guo, L. Glavas and A. C. Albertsson, Prog. Polym. Sci., 2013, 38, 1263.
J. G. Hardy, D. J. Mouser, N. Arroyo-Currás, S. Geissler, J. K. Chow, L. Nguy, J. M. Kim and C. E. Schmidt, J. Mater. Chem. B, 2014, 2, 6809.
D. Svirskis, J. Travas-Sejdic, A. Rodgers and S. Garg, J. Control. Release, 2010, 146, 6.
V. Pillay, T. S. Tsai, Y. E. Choonara, L. C. du Toit, P. Kumar, G. Modi, D. Naidoo, L. K. Tomar, C. Tyagi and V. M. Ndesendo, J. Biomed. Mater. Res., A, 2014, 102, 2039.
R. Dong, Y. Zhou, X. Huang, X. Zhu X, Y. Lu and J. Shen. Advanced Materials, 2015, 27, 498.
A. R. Hirst, B. Escuder, J. F. Miravet and D. K. Smith, Angew. Chem. Int. Ed., 2008, 47, 8002.
M. Hasegawa and M. Iyoda, Chem. Soc. Rev., 2010, 39, 2420.
S. H. Kim and J. R. Parquette, Nanoscale, 2012, 4, 6940.
A. J. Hodgson, K. Gilmore, C. Small, G. G. Wallace, I. L. Mackenzie, T. Aoki and N. Ogata, Supramol. Sci., 1994, 1, 77.
E. K. Schillinger, E. Mena-Osteritz, J. Hentschel, H. G. Borner and Peter Bauerle, Adv. Mater. 2009, 21, 1562.
A. Digennaro, H. Wennemers, G. Joshi, S. Schmid, E. Mena-Osteritz and Peter Bauerle, Chem. Commun., 2013, 49, 10929.
Z. Zhang, S. Wei and L. Han, Adv. Mater. Res., 2011, 284-286, 2110.
I. Rozalska, P. Kulyk and I. Kulszewicz-Bajer, New. J. Chem., 2004, 28, 1235.
I. Kulszewicz-Bajer, I. Rozalska and M. Kurlyek, New. J. Chem., 2004, 28, 669.
G. J. M. Habraken, M. Peeters, C. H. J. T. Dietz, C. E. Koninga and A. Heise, Polym. Chem., 2010, 1, 514.
Z. Pang, J. Fu, P. Lv, F. Huang and Q. Wei, Sensors, 2014, 14, 21453.
U. Slotta, M. Tammer, F. Kremer, P. Koelsch and T. Scheibel, Supramol. Chem., 2006, 18, 1.
F. Paquet-Mercier, T. Lefevre, M. Auger and M. Pezolet, Soft Matter, 2013, 9, 208.
O. S. Rabotyagova, P. Cebe and D. L. Kaplan, Macromol. Biosci. 2010, 10, 49.
J. G. Hardy and T. R. Scheibel, J. Polym. Sci. A: Polym. Chem. 2009, 47, 3957-3963.
J. G. Hardy and T. R. Scheibel, Biochem. Soc. Trans. 2009, 37, 677.
J. G. Hardy, A. Leal-Egaña and T. R. Scheibel, Macromol. Biosci., 2013, 13, 1431.
Z. Shao, Z. Yu, Jianchen Hu, S. Chandrasekaran, D. M. Lindsay, Z. Wei and C. F. J. Faul, J. Mater. Chem., 2012, 22, 16230.
Y. Wang, H. D. Tran, L. Liao, X. Duan, and R. B. Kaner, J. Am. Chem. Soc., 2010, 132, 10365.
C. Gabriel, S. Gabriel and E. Corthout, Phys. Med. Biol., 1996, 41, 2231.
S. Gabriel, R. W. Lau and C. Gabriel, Phys. Med. Biol., 1996, 41, 2251.
108 S. Gabriel, R. W. Lau and C. Gabriel, Phys. Med. Biol., 1996, 41, 2271.
P. H. Zeplin, N. C. Maksimovikj, M. C. Jordan, J. Nickel, G. Lang, A. H. Leimer, L. Römer and T. Scheibel, Adv. Funct. Mater., 2014, 24, 2658.
C. Vallejo-Giraldo, A. Kelly, M. J. Biggs, Drug. Discov. Today, 2014, 19, 88.
H. Shin, S. Jo and A. G. Mikos, Biomaterials, 2003, 24, 4353.
K. G. Sreejalekshmi and P. D. Nair, J. Biomed. Mater. Res. Part A, 2011, 96A, 477.
K. I. Umehara, T Iwatsubo, K. Noguchi, T. Usui and H. Kamimura, Xenobiotica, 2008, 38, 1203.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

We claim:

1. An electroactive supramolecular polymeric assembly, comprising: an electroactive ABA block copolymer, where A is a non-electroactive polymer and B is an electroactive polymer, wherein the polymer has the following structure:

where n is 2 to 1000 and m+p is 2 to 2000.

2. The assembly of claim 1, wherein n is 2 and m+p is 10 or n is 4 and n+p is 26.

3. The assembly of claim 1, further comprising an agent.

4. The assembly of claim 3, wherein the agent is selected from the group consisting of: a drug, a therapeutic agent, a radiological agent, a chemological agent, a small molecule drug, a biological agent, and a combination thereof.

* * * * *